United States Patent
Hudlicky et al.

(10) Patent No.: US 9,475,823 B2
(45) Date of Patent: Oct. 25, 2016

(54) METHODS FOR THE PREPARATION OF HYDROMORPHONE

(71) Applicants: Tomas Hudlicky, St. Catherines (CA); Mary Ann Endoma-Arias, St. Catharines (CA); Brennan Augusta Murphy, St. Catharines (CA); Ivan Snajdr, Prague (CZ); Ales Machara, Prague (CZ)

(72) Inventors: Tomas Hudlicky, St. Catherines (CA); Mary Ann Endoma-Arias, St. Catharines (CA); Brennan Augusta Murphy, St. Catharines (CA); Ivan Snajdr, Prague (CZ); Ales Machara, Prague (CZ)

( * ) Notice: Subject to any disclaimer, the term of this patent is extended or adjusted under 35 U.S.C. 154(b) by 0 days.

(21) Appl. No.: 14/615,892

(22) Filed: Feb. 6, 2015

(65) Prior Publication Data

US 2015/0225419 A1  Aug. 13, 2015

Related U.S. Application Data

(60) Provisional application No. 61/937,126, filed on Feb. 7, 2014.

(51) Int. Cl.
C07D 489/02 (2006.01)
C07D 491/20 (2006.01)
C07D 495/18 (2006.01)

(52) U.S. Cl.
CPC .......... *C07D 495/18* (2013.01); *C07D 489/02* (2013.01)

(58) Field of Classification Search
USPC .............................. 546/45, 15, 39
See application file for complete search history.

(56) References Cited

U.S. PATENT DOCUMENTS 7,928,234 B2  4/2011  Carroll et al.

*Primary Examiner* — Charanjit Aulakh
(74) *Attorney, Agent, or Firm* — Parker Highlander PLLC

(57) ABSTRACT

The present application relates to methods for the preparation of morphine derivatives. In particular, the present application relates to methods for the preparation of hydromorphone from oripavine and oripavine from thebaine.

14 Claims, No Drawings

METHODS FOR THE PREPARATION OF HYDROMORPHONE

CROSS-REFERENCE TO RELATED APPLICATIONS

The present application claims the benefit of priority from U.S. provisional patent application No. 61/937,126, filed on Feb. 7, 2014, the contents of which are incorporated herein by reference in their entirety.

FIELD

The present application relates to methods for the preparation of morphine derivatives. In particular, the present application relates to methods for the preparation of hydromorphone from oripavine and oripavine from thebaine.

BACKGROUND

The use of thebaine and oripavine as starting materials for the commercial production of semisynthetic opiate-derived agents has been reported.[1,2,3,4,5] For example, methods for the preparation of morphine derivatives from thebaine are known. U.S. Pat. No. 7,928,234 discloses methods for the conversion of thebaine to morphine derivatives via ketal intermediates.

These compounds can be medicinally useful because of their high therapeutic value and low abuse potential.[6,7,8] Engineered poppy plants[9,10] have been cultivated to express thebaine in high quantities in recent years for use as a starting material for the downstream production of semisynthetic opiates. A scalable method for the transformation of thebaine to oripavine, may be useful to shorten and/or generalize industrial preparations of semi-synthetic opioid derivatives.

Known conditions for 3-O-demethylation of buprenorphine derivatives having an origin in thebaine are harsh, involving long reaction times and strongly alkaline systems at high temperatures, 100-200° C.[2]

The conversion of thebaine to oripavine using known methods of O-demethylation have failed. For example, in contrast to other opiate derivatives, the desired O-demethylated product was not recovered from the reaction of thebaine with thiolate.[11] To date, 3-O-demethylation of thebaine to produce oripavine has only been accomplished by L-Selectride, albeit in low yield (35%) and long reaction times (14 days).[12,13,14] Though this represents a direct method, alternatives to the use of L-Selectride are still being sought.

SUMMARY

In the studies of the present application a method for the preparation of hydromorphone from oripavine is disclosed. The synthesis of oripavine from thebaine using either an iron-pentacarbonyl or thioaldehyde protection route is also disclosed in the present studies.

Accordingly, the present application includes a method for the preparation of hydromorphone, comprising:

(a) protecting oripavine under conditions to provide a ketal of Formula I:

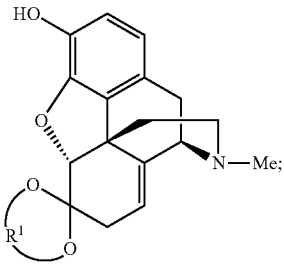

(b) reducing the ketal of Formula I under conditions to provide a ketal of Formula II:

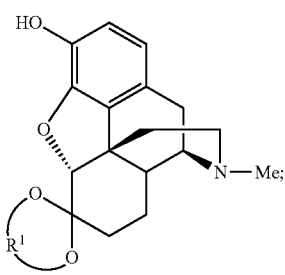

and (c) deprotecting the ketal of Formula II under conditions to provide hydromorphone, wherein $R^1$, together with the oxygen atoms to which it is bonded, forms a hydrolysable cyclic protecting group.

In an embodiment, the oripavine is prepared by a method comprising:

(a) protecting the cyclohexadiene moiety of thebaine under conditions to provide a cyclo hexadiene-protected thebaine;

(b) 3-O-demethylating the cyclohexadiene-protected thebaine under conditions to provide a cyclohexadiene-protected oripavine; and (c) deprotecting the cyclohexadiene-protected oripavine under conditions to provide oripavine.

Other features and advantages of the present application will become apparent from the following detailed description. It should be understood, however, that the detailed description and the specific examples while indicating embodiments of the application are given by way of illustration only, since various changes and modifications within the spirit and scope of the application will become apparent to those skilled in the art from this detailed description.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The expression "proceed to a sufficient extent" as used herein with reference to the reactions or method steps disclosed herein means that the reactions or method steps proceed to an extent that conversion of the starting material or substrate to product is maximized. Conversion may be maximized when greater than about 5, 10, 15, 20, 25, 30, 35, 40, 45, 50, 55, 60, 65, 70, 75, 80, 85, 90, 95 or 100% of the starting material or substrate is converted to product.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "an acid" should be understood to present certain aspects with one acid or two or more additional acids.

In embodiments comprising an "additional" or "second" component, such as an additional or second acid, the second component as used herein is chemically different from the other components or first component. A "third" component is different from the other, first, and second components, and further enumerated or "additional" components are similarly different.

In embodiments of the present application, the compounds in the methods described herein have at least one asymmetric center. Where compounds possess more than one asymmetric center, they may exist as diastereomers. It is to be understood that all such isomers and mixtures thereof in any proportion are encompassed within the scope of the methods of the present application. It is to be further understood that while the stereochemistry of the compounds in the methods may be as shown in any given compound listed herein, such compounds may also contain certain amounts (e.g. less than 20%, suitably less than 10%, more suitably less than 5%) of compounds having alternate stereochemistry.

The term "protecting" as used herein refers to using a chemical moiety, i.e. a "protecting group" which protects or masks a reactive portion of a molecule to prevent side reactions in that reactive portion of the molecule, while manipulating or reacting a different portion of the molecule. After the manipulation or reaction is complete, the protecting group is removed under conditions that do not degrade or decompose the remaining portions of the molecule; i.e. the protected reactive portion of the molecule is "deprotected". The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, $3^{rd}$ Edition, 1999 and in Kocienski, P. Protecting Groups, 3rd Edition, 2003, Georg Thieme Verlag (The Americas).

The term "hydrolysable cyclic protecting group" as used herein refers to a protecting group that masks a reactive portion of a molecule by forming a cyclic ring structure that can be removed under hydrolysis conditions. The hydrolysis conditions may be basic or acidic conditions, and in an embodiment are acidic hydrolysis conditions.

THF as used herein refers to tetrahydrofuran.

The term "oripavine" as used herein refers to a compound of the following formula:

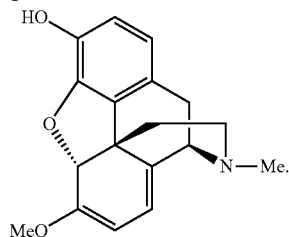

The term "hydromorphone" as used herein refers to a compound of the following formula:

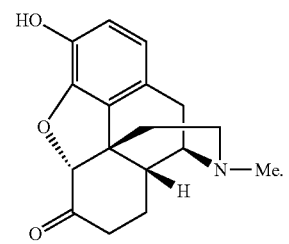

The term "thebaine" as used herein refers to a compound of the following formula:

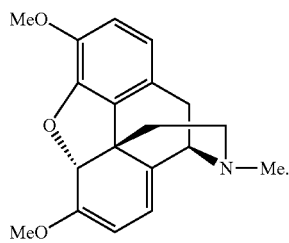 [SMILES: COC1=CC=C2[C@H]3Cc4ccc(O)c5c4[C@@]2(CCN3C)[C@H]1O5]

II. Methods

In the studies of the present application a method for the preparation of hydromorphone from oripavine is disclosed. In contrast to known methods for the preparation of hydromorphone from thebaine, the methods of the present application do not comprise an O-demethylation step. The synthesis of oripavine from thebaine in three steps using either an iron-pentacarbonyl or thioaldehyde protection route is also disclosed in the present studies. This synthetic sequence may be useful in the large-scale conversion of thebaine to oripavine.

Accordingly, the present application includes a method for the preparation of hydromorphone, comprising:

(a) protecting oripavine under conditions to provide a ketal of Formula I:

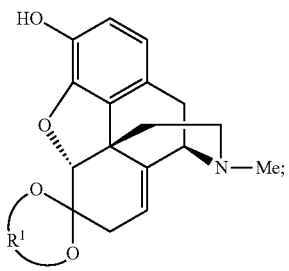

I (b) reducing the ketal of Formula I under conditions to provide a ketal of Formula II:

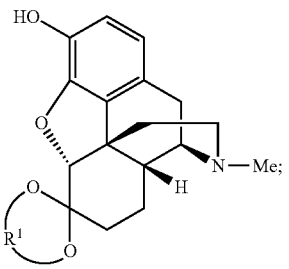

II and
(c) deprotecting the ketal of Formula II under conditions to provide hydromorphone,
wherein $R^1$, together with the oxygen atoms to which it is bonded, forms a hydrolysable cyclic protecting group.

The conditions to provide the ketal of Formula I may vary and the selection of suitable conditions can be made by a person skilled in the art. In an embodiment, the conditions to provide the ketal of Formula I comprise adding a suitable acid catalyst, such as p-toluenesulfonic acid, to a stirred suspension or solution comprising the oripavine, a suitable difunctional alcohol such as ethylene glycol and optionally a solvent, such as benzene, and allowing the mixture to react for a time and temperature for the conversion of the oripavine to the ketal of Formula I to proceed to a sufficient extent, for example at a temperature of about 60° C. to about 100° C. or about 80° C. for a time of about 10 minutes to about 2 hours or about 30 minutes, followed by a suitable workup.

In an embodiment of the present application, $R^1$ is $C_{1-6}$alkylene. In a further embodiment, $R^1$ is $C_{1-4}$alkylene.

In another embodiment, the difunctional alcohol is ethylene glycol. In this embodiment, $R^1$, together with the oxygen atoms to which it is bonded, and the carbon atom to which each oxygen atom is bonded, forms a dioxolane moiety.

The conditions to provide the ketal of Formula II may vary and the selection of suitable conditions can be made by a person skilled in the art. In an embodiment, the conditions comprise reducing the ketal of Formula I under hydrogenation conditions for a time and temperature for the conversion of the ketal of Formula I to the ketal of Formula II to proceed to a sufficient extent. It will be appreciated by a person skilled in the art that the hydrogenation conditions can comprise any of the known methods for the hydrogenation of the double bond of the C-ring of the oripavine ketal that do not otherwise react with or degrade the other functional groups in the oripavine ketal.

For example, the hydrogenation conditions can comprise transfer hydrogenation or the use of hydrogen gas in the presence of a catalyst, such as Pt/C, Pd/C or any of the well-known transition metal hydrogenation catalysts, or by the use of diimide. Suitable solvents, reaction temperatures and reactant ratios can be selected by a person skilled in the art. For example, solvents useful in the hydrogenation reaction include alcohols such as methanol, ethanol, isopropanol, n-butanol and 1-octanol, water, aqueous solutions of mineral acids and aqueous organic acids, such as formic acid and acetic acid and mixtures thereof.

In an embodiment of the present application, the conditions to provide the ketal of Formula II comprise reacting the ketal of Formula I with hydrogen gas, for example at about 1 atmosphere pressure or any other suitable pressure, in a suitable solvent such as methanol in the presence of a suitable hydrogenation catalyst such as Pt/C and allowing the mixture to react for a time and temperature for the conversion of the ketal of Formula I to the ketal of Formula II to proceed to a sufficient extent, for example at a temperature of about 0° C. to about 40° C. or about 20° C. to about 25° C. for a time of about 1 hour to about 4 days or about 48 hours, followed by a suitable workup.

The conditions to provide hydromorphone may vary and the selection of suitable conditions can be made by a person skilled in the art. In an embodiment, the conditions to provide hydromorphone comprise deprotecting the ketal of Formula II under suitable acidic conditions for a time and temperature for the conversion of the ketal of Formula II to hydromorphone to proceed to a sufficient extent, for example at a temperature of about 60° C. to about 100° C. or about 80° C. for a time of about 2 hours to about 8 hours or about 4 hours, followed by a suitable workup. It is an embodiment that the suitable acidic conditions comprise adding a suitable acid such as a mineral acid, for example, about 1 N to about 6 N or about 3 N HCl, to a solution of the ketal of Formula II in a suitable organic solvent, such as THF.

In another embodiment, the hydromorphone is prepared from the oripavine in a one-pot synthesis without the isolation of intermediates. In an embodiment, the reducing and deprotecting steps of the method of the present application are carried out as a one-pot procedure. For example, subsequent to the step of reducing the ketal of Formula I, the reaction mixture is filtered to remove the hydrogenation catalyst, the solvent is evaporated, and the residue comprising the ketal of Formula II is subjected to the deprotecting step.

In an embodiment, the oripavine is prepared by a method comprising:
(a) protecting the cyclohexadiene moiety of thebaine under conditions to provide a cyclohexadiene-protected thebaine;
(b) 3-O-demethylating the cyclohexadiene-protected thebaine under conditions to provide a cyclohexadiene-protected oripavine; and
(c) deprotecting the cyclohexadiene-protected oripavine under conditions to provide oripavine.

The conditions to provide the cyclohexadiene-protected thebaine may vary and the selection of suitable conditions can be made by a person skilled in the art. In an embodiment, the cyclohexadiene moiety of thebaine is protected by an iron tricarbonyl group and the method comprises:
(a) protecting the cyclohexadiene moiety of thebaine under conditions to provide a cyclohexadiene-protected thebaine of Formula III:

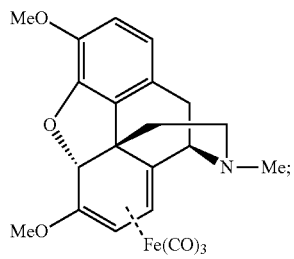

III (b) 3-O-demethylating the cyclohexadiene-protected thebaine of Formula III under conditions to provide a cyclohexadiene-protected oripavine of Formula IV:

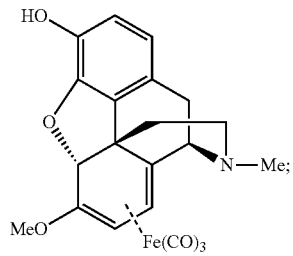

IV and
(c) deprotecting the cyclohexadiene-protected oripavine of Formula IV under conditions to provide oripavine.

The conditions to provide the cyclohexadiene-protected thebaine of Formula III may vary and the selection of suitable conditions can be made by a person skilled in the art. In an embodiment, the conditions to provide the cyclohexadiene-protected thebaine of Formula III comprise irradiating thebaine and iron pentacarbonyl with ultraviolet light in a suitable organic solvent such as benzene for a time and temperature for the conversion of thebaine to the cyclohexadiene-protected thebaine of Formula III to proceed to a sufficient extent, for example at a temperature of about 20° C. to about 60° C. or about 40° C. for a time of about 1 hour to about 4 days or about 48 hours, followed by a suitable workup.

The conditions to 3-O-demethylate the cyclohexadiene-protected thebaine to provide the cyclohexadiene-protected oripavine of Formula IV are selected from any of the well-known methods to demethylate an aromatic methoxy group and the selection of suitable conditions can be made by a person skilled in the art. For example, demethylation methods comprise the use of Lewis acids such as $BBr_3$ and $BF_3.SMe_2$, mixed mineral acids such as methanesulfonic acid, oxidants, reductants, as well as boron, silica and aluminum compounds.

The conditions to deprotect the cyclohexadiene-protected oripavine of Formula IV to provide the oripavine may vary and the selection of suitable conditions can be made by a person skilled in the art. In an embodiment, the conditions to provide the oripavine from the cyclohexadiene-protected oripavine of Formula IV comprise irradiating a dispersion of the cyclohexadiene-protected oripavine of Formula IV in a suitable solvent such as acetonitrile with ultraviolet light for a time and temperature for the conversion of the cyclohexadiene-protected oripavine of Formula IV to oripavine to proceed to a sufficient extent, for example at a temperature of about 20° C. to about 60° C. or about 40° C. for a time of about 1 hour to about 3 hours or about 2.5 hours, followed by a suitable workup.

In another embodiment, the cyclohexadiene moiety of thebaine is protected as a Diels-Alder adduct of thioaldehyde and the method comprises:
(a) protecting the cyclohexadiene moiety of thebaine under conditions to provide one or more cyclohexadiene-protected thebaines of Formula V(a) or V(b):

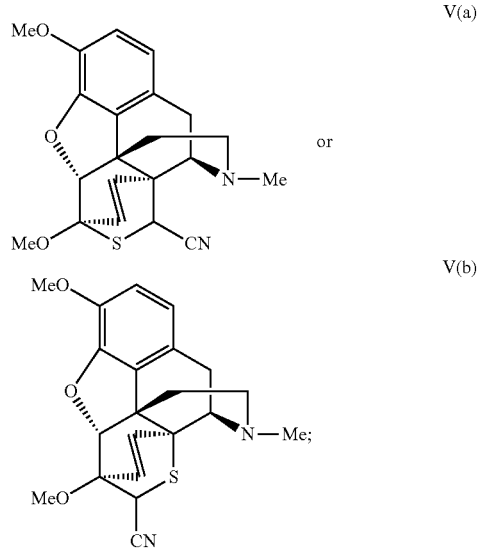

V(a)

or

V(b)

(b) 3-O-demethylating one or more of the cyclohexadiene-protected thebaines of Formula V(a) or V(b) under conditions to provide one or more cyclohexadiene-protected oripavines of Formula VI(a) or VI(b):

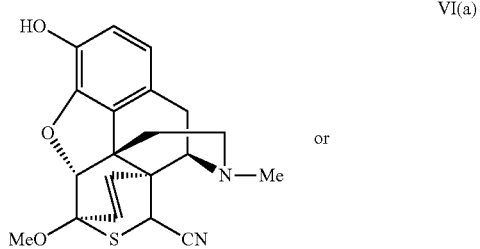

VI(a)

or

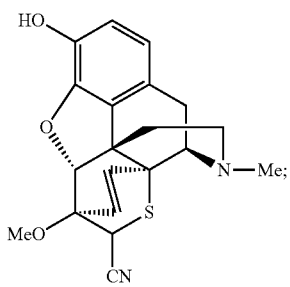

and (c) deprotecting one or more of the cyclohexadiene-protected oripavines of Formula VI(a) or VI(b) under conditions to provide oripavine.

It will be appreciated by a person skilled in the art that in the methods of the present application, 3-O-demethylation of the compound of Formula V(a) provides the compound of Formula VI(a), and 3-O-demethylation of the compound of Formula V(b) provides the compound of Formula VI(b).

The conditions to provide the one or more cyclohexadiene-protected thebaines of Formula V(a) or V(b) may vary and the selection of suitable conditions can be made by a person skilled in the art. In an embodiment, the conditions to provide the one or more cyclohexadiene-protected thebaines of Formula V(a) or V(b) comprise dispersing thebaine, calcium chloride dihydrate and sodium S-(cyanomethyl) sulfothioate in a suitable solvent system such as a mixture of methanol and benzene, adding a suitable base such as triethylamine and allowing the mixture to react for a time and temperature for the conversion of the thebaine to the one or more cyclohexadiene-protected thebaines of Formula V(a) or V(b) to proceed to a sufficient extent, for example at a temperature of about 0° C. to about 40° C. or about 20° C. to about 25° C. for a time of about 1 hour to about 1 day or about 8 hours, followed by a suitable workup.

Again, the conditions to 3-O-demethylate the cyclohexadiene-protected thebaine to provide the one or more cyclohexadiene-protected oripavines of Formula VI(a) or VI(b) are selected from any of the well-known methods to demethylate an aromatic methoxy group and the selection of suitable conditions can be made by a person skilled in the art. For example, demethylation methods comprise the use of Lewis acids such as BBr$_3$ and BF$_3$.SMe$_2$, mixed mineral acids such as methanesulfonic acid, oxidants, reductants, as well as boron, silica and aluminum compounds.

The conditions to deprotect the cyclohexadiene-protected oripavines of Formula VI(a) or VI(b) to provide the oripavine may vary and the selection of suitable conditions can be made by a person skilled in the art.

In an embodiment, the conditions to provide the oripavine from the one or more cyclohexadiene-protected oripavines of Formula VI(a) or VI(b) comprise adding 2,6-di-tert-butyl-4-methylphenol and 2,3-dimethylbutadiene to a solution of the one or more cyclohexadiene-protected oripavines of Formula VI(a) or VI(b) in a suitable solvent such as DMSO and allowing the mixture to react for a time and temperature for the conversion of the one or more cyclohexadiene-protected oripavines of Formula VI(a) or VI(b) to the oripavine to proceed to a sufficient extent, for example at a temperature of about 50° C. to about 100° C. or about 75° C. for a time of about 1 hour to about 2 days or about 24 hours, followed by a suitable workup.

In another embodiment, the conditions to provide the oripavine from the one or more cyclohexadiene-protected oripavines of Formula VI(a) or VI(b) comprise adding mCPBA to a solution of the one or more cyclohexadiene-protected oripavines of Formula VI(a) or VI(b) in a suitable organic solvent such as dichloromethane and allowing the mixture to react for a time and temperature for the conversion of the one or more cyclohexadiene-protected oripavines of Formula VI(a) or VI(b) to the oripavine to proceed to a sufficient extent, for example at a temperature of about 0° C. to about 40° C. or about 20° C. to about 25° C. for a time of about 1 hour to about 1 day or about 12 hours, followed by a suitable workup.

It will be appreciated by a person skilled in the art that in the methods of the present application, 3-O-demethylation of the compound of Formula V(a) provides the compound of Formula VI(a):

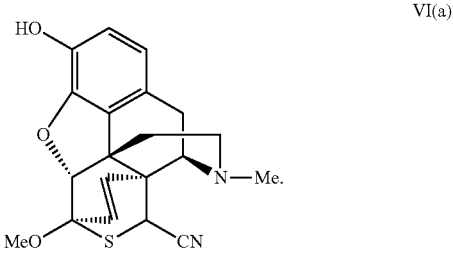 [SMILES: CO[C@]12C=C[C@@]3(C(C#N)S1)[C@H]1Cc4ccc(O)c5c4[C@@]3(CCN1C)[C@H]2O5]

It will also be appreciated by a person skilled in the art that in the methods of the present application, 3-O-demethylation of the compound of Formula V(b) provides the compound of Formula VI(b):

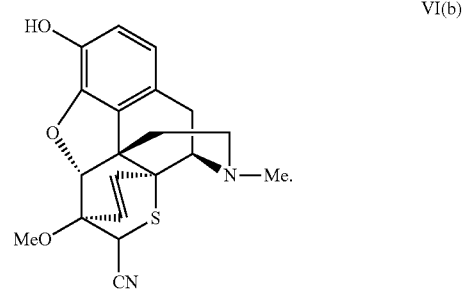 [SMILES: CO[C@]12C=C[C@@]3(SC1C#N)[C@H]1Cc4ccc(O)c5c4[C@@]3(CCN1C)[C@H]2O5]

In another embodiment, the oripavine is prepared from the thebaine in a one-pot synthesis without the isolation of intermediates.

The present application also includes a method for the preparation of hydromorphone, comprising:

(a) protecting the cyclohexadiene moiety of thebaine under conditions to provide a cyclohexadiene-protected thebaine;

(b) 3-O-demethylating the cyclohexadiene-protected thebaine under conditions to provide a cyclohexadiene-protected oripavine;

(c) deprotecting the cyclohexadiene-protected oripavine under conditions to provide oripavine;

(d) protecting oripavine under conditions to provide a ketal of Formula I:

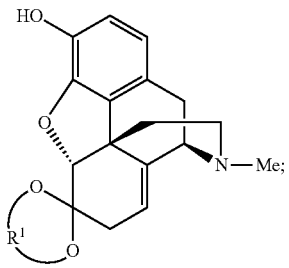

(e) reducing the ketal of Formula I under conditions to provide a ketal of Formula II:

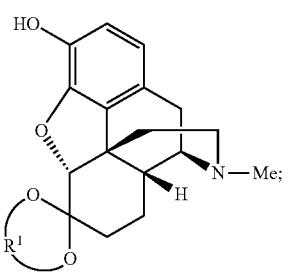

and (f) deprotecting the ketal of Formula II under conditions to provide hydromorphone, wherein $R^1$, together with the oxygen atoms to which it is bonded, forms a hydrolysable cyclic protecting group.

In an embodiment, the hydromorphone is prepared from the thebaine in a one-pot synthesis without the isolation of intermediates. In another embodiment, at least a portion of the method for the preparation of hydromorphone from thebaine is carried out as a one-pot synthesis.

III. Compounds

The intermediate thioaldehyde adduct isomers prepared in the studies of the present application are new. Accordingly, the present application also includes a compound of Formula VII(a) or VII(b):

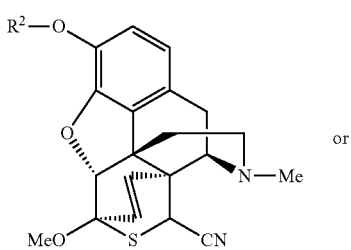

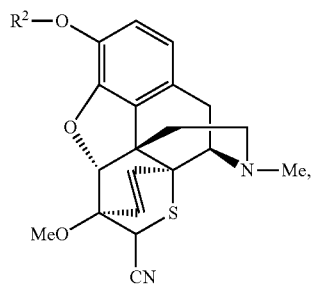

wherein $R^2$ is H or $CH_3$.

In an embodiment, the compound of Formula VII(a) or VII(b) is a compound of Formula VII(a). In another embodiment, the compound of Formula VII(a) or VII(b) is a compound of Formula VII(b).

In an embodiment, $R^2$ is H. In another embodiment, $R^2$ is $CH_3$.

The following non-limiting examples are illustrative of the present application:

EXAMPLES

Example 1

Preparation of Hydromorphone from Oripavine

I. Preparation of Oripavine Ketal

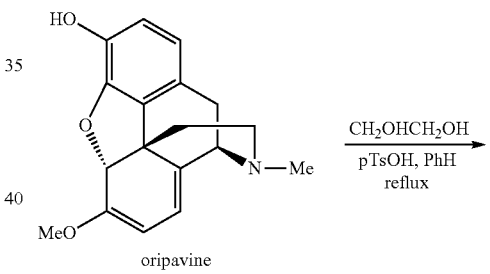

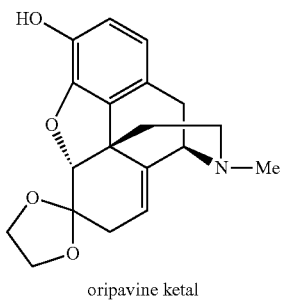

To a stirred suspension of oripavine (100 mg, 0.34 mmol) in benzene (PhH; 1.5 mL) and ethylene glycol (1 mL) was added p-toluenesulfonic acid monohydrate (pTsOH.$H_2$O; 150 mg, 0.80 mmol). The mixture was heated to reflux for 30 min, and then allowed to reach room temperature. The reaction mixture was then added to a stirred mixture of ethyl acetate (EtOAc; 10 mL) and saturated NaHCO$_3$ (10 mL). The layers were separated and the aqueous layer was further extracted with EtOAc (3×5 mL). The combined organic extracts were dried over MgSO$_4$, filtered and concentrated via rotary evaporation to a yellow residue which was used as is in the next step.

The use of monofunctional alcohols such as methanol was also explored but was not found to be useful in the method of the present studies.

II. Preparation of Hydromorphone Ketal

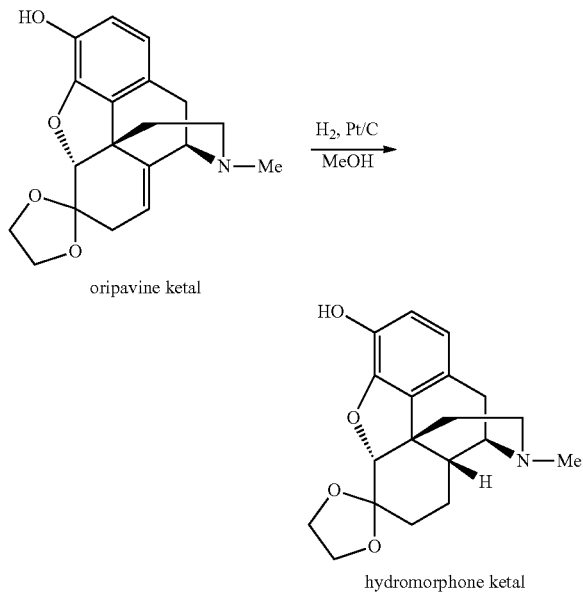

To a stirred solution of crude oripavine ketal in MeOH (3 mL) from step I above was added 5% Pt on C (6 mg). The flask containing the reaction mixture was evacuated/refilled with $H_2$ gas three times. The reaction mixture was then stirred under an atmosphere of $H_2$ gas for 48 h. The catalyst was removed by filtration through Celite™. The filtrate was concentrated using rotary evaporation to afford a crude residue of hydromorphone ketal which was used with no further purification in the next step.

III. Preparation of Hydromorphone

To a stirred solution of crude hydromorphone ketal from step II above in THF (5 mL) was added 3 N HCl (2.5 mL). The mixture was heated to 80° C. for 4 h, and then allowed to reach room temperature. The mixture was concentrated via rotary evaporation to remove THF. A saturated solution of $NaHCO_3$ was added to adjust the pH of the mixture to 8. It was then extracted with $CH_2Cl_2$ (3×10 mL). The combined organic extracts were dried over $MgSO_4$, filtered and concentrated via rotary evaporation to a solid residue. Chromatography of the residue on silica gel using a mixture of $CH_2Cl_2$ and MeOH (6:1) afforded hydromorphone as a white solid (41 mg, 42.7% yield, over 3 steps).

Example 2

Preparation of Oripavine from Thebaine

The method of the present study employs protection of the cyclohexadiene moiety in thebaine with either iron(0)-pentacarbonyl[15,16] or as a thioaldehyde-Diels-Alder adduct,[17,18,19,20] both serving to prevent the acid-catalyzed apomorphine rearrangement or enone formation.[13,21]

Experimental

A. Preparation of Oripavine Using Iron Tricarbonyl Protection

I. Preparation of Thebaine Iron Tricarbonyl

Thebaine iron tricarbonyl was prepared by the previously published method by Birch.[15] Thebaine (2 g, 6.4 mmol) was dispersed in benzene (20 mL), the solution was degassed by bubbling with argon for 3 min and iron pentacarbonyl (5 mL, 37 mmol) was added. The mixture was then irradiated in a UV reactor for 48 hours at 40° C. The reaction mixture was then concentrated in vacuo and purified by column chromatography (10:1 $CH_2Cl_2$:MeOH). Purified product was recrystallized from absolute ethanol. Spectral data were in agreement with previously published data.[15] Yield: 95%; an orange solid.

$R_f$=0.81 (10:1 $CH_2Cl_2$:MeOH); mp 126-127° C. (EtOH); $[\alpha]_D$=−188° (c=0.0128 g/ml, $CHCl_3$); $^1H$ NMR (300 MHz, $CDCl_3$) δ 6.68 (d, J=8.0 Hz, 1H), 6.59 (d, J=7.8 Hz, 1H), 5.32 (d, J=3.5 Hz, 1H), 4.92 (s, 1H), 4.55 (d, J=4.4 Hz, 1H), 3.82 (s, 3H), 3.58 (s, 3H), 3.24 (d, J=17.7 Hz, 1H), 3.00 (d, J=6.0 Hz, 1H), 2.81-2.16 (m, 7H), 1.66 (d, J=12.4 Hz, 2H). $^{13}C$ NMR (75 MHz, $CDCl_3$) δ 211.88, 143.52, 142.76, 137.91, 126.46, 120.41, 116.31, 112.94, 87.88, 77.25, 74.96, 61.85, 56.93, 56.33, 47.82, 45.37, 42.99, 35.19, 29.17; IR (neat, cm$^{-1}$) v 2930, 2030, 1975, 1942, 1626, 1500, 1436, 1326, 1207; MS (EI$_+$, m/z (rel. %)): 451 (10), 395 (55), 311 (50), 254 (100), 239 (80), 211 (23), 83 (30), 42 (35); HRMS (EI) calcd. for $C_{22}H_{21}FeNO_6$: 451.07179. found 451.07033.

II. Preparation of Oripavine Iron Tricarbonyl

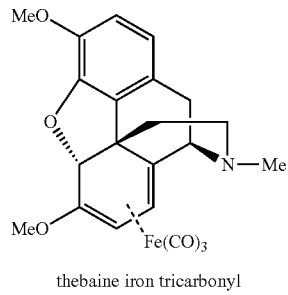

thebaine iron tricarbonyl

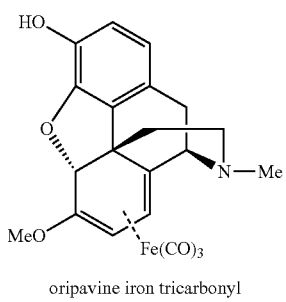

oripavine iron tricarbonyl

Method A: To a solution of thebaine iron tricarbonyl (200 mg, 0.44 mmol) in dry $CH_2Cl_2$ (20 mL) was slowly added BBr$_3$ (0.66 g, 2.6 mmol) at 0° C. under an argon atmosphere. The reaction was stirred for 20 min at 0° C., removed from the ice bath and stirred for another 15 min. The reaction mixture was poured into cold water and the acidity was slowly adjusted to pH=6 with 15% aqueous NaOH solution. The mixture was then extracted with $CH_2Cl_2$/IPA (10/1) four times. The combined organic phases were concentrated in vacuo and purified by column chromatography ($CH_2Cl_2$: MeOH, 7:1) yielding oripavine iron tricarbonyl (160 mg, 83%) as a dark green solid.

Method B: To a solution of thebaine iron tricarbonyl (200 mg, 0.44 mmol) in dry $CH_2Cl_2$ (20 mL) was slowly added BF$_3$.SMe$_2$ complex (0.28 mL, 2.67 mmol) at 0° C. under an argon atmosphere. The reaction was stirred for 4 hours at 0° C., removed from the ice bath and stirred for another 1.5 hours. The quenching and workup procedure was the same as method A, yielding oripavine iron tricarbonyl (160 mg, 83%).

Method C: To a solution of thebaine iron tricarbonyl (183 mg, 0.41 mmol) in dry MeSO$_3$H (3.0 mL, 48.8 mmol) was slowly added methionine (213 mg, 1.42 mmol). The orange solution was then heated to 50° C. and left to stir for 28 hours. The reaction was monitored by HPLC. The reaction was quenched and the product isolated in the same fashion as methods A and B, yielding oripavine iron tricarbonyl (120 mg, 67%).

Method D: To a solution of thebaine iron tricarbonyl (90 mg, 0.2 mmol) in dry $CH_2Cl_2$ (5 mL) was slowly added B-I-9-BBN 1M in hexanes (0.4 mL, 0.4 mmol) at room temperature. After two hours, the reaction was quenched and the product isolated in the same fashion as previously described in methods A to C to yield oripavine iron tricarbonyl (61 mg, 70%).

Dark green solid; $R_f$=0.52 (10:1 $CH_2Cl_2$: MeOH); $^1$H NMR (300 MHz, CDCl$_3$) δ 6.67 (s, 1H), 6.54 (s, 1H), 5.31 (s, 1H), 4.91 (s, 1H), 4.54 (s, 1H), 3.58 (s, 3H), 3.20 (s, 1H), 3.02 (s, 1H), 2.83-2.15 (m, 7H), 1.66 (s, 2H); $^{13}$C NMR (75 MHz, CD$_3$OD) δ 211.98, 142.43, 139.32, 137.79, 124.94, 120.36, 116.71, 116.48, 87.76, 76.56, 76.39, 75.24, 61.87, 55.71, 45.07, 41.57, 34.43, 29.02; IR (neat, cm$^{-1}$) v 2915, 2036, 1948, 1613, 1444, 1207, 1145; MS (EI$_+$, m/z (rel. %)): 437 (70), 381 (70), 353 (100), 325 (23), 297 (40), 281 (22); HRMS (EI) calcd. for $C_{21}H_{19}FeNO_6$: 437.05484. found 437.05614.

III. Preparation of Oripavine from Oripavine Iron Tricarbonyl

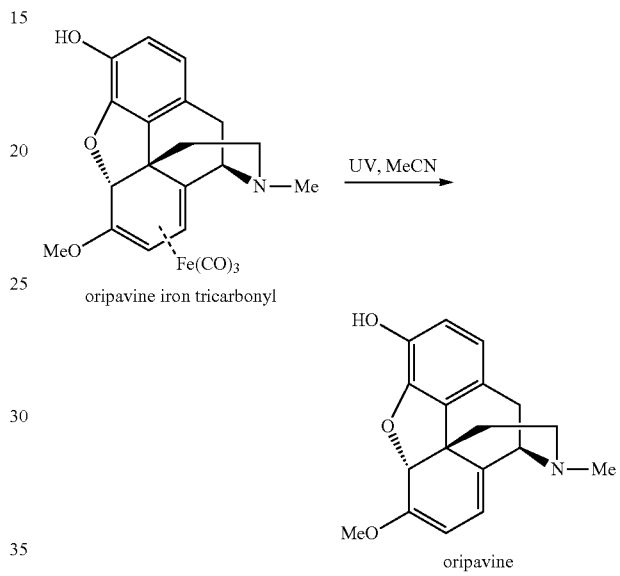

Oripavine iron tricarbonyl (60 mg, 0.137 mmol) was dispersed in acetonitrile (5 mL), the solution degassed by bubbling with argon for 3 min and then UV irradiated for 2.5 hours at 40° C. The reaction mixture was then concentrated in vacuo and purified by column chromatography (6:1 $CH_2Cl_2$: MeOH) yielding 18 mg (35%) of recovered starting material and 14 mg (30%) of oripavine. The spectral data for oripavine were in agreement with previously published data.[14]

B. Preparation of Oripavine Using Thioaldehyde-Diels-Alder Adduct Protection

I. Preparation of Sodium S-(Cyanomethyl) Sulfothioate Bunte Salt

A mixture of Na$_2$S$_2$O$_3$.5H$_2$O (9.97 g, 63 mmol), chloroacetonitrile (5 g, 66 mmol), in water (20 mL) and ethanol (20 mL) was heated at 80° C. for 1 hour, then left at room temperature overnight. The mixture was cooled to 0° C. and then filtered, and rinsed with ethanol. The product was recrystallized from hot ethanol and dried in vacuo to yield the Bunte salt (7.06 g, 64%).

II. Preparation of Thioaldehyde Adduct Isomers

Thebaine (930 mg, 3 mmol), calcium chloride dihydrate (620 mg, 4.2 mmol), and sodium S-(cyanomethyl) sulfothioate (735 mg, 4.2 mmol) were dispersed in benzene (7 mL) and methanol (7 mL) and stirred vigorously. Triethylamine (420 mg, 4.2 mmol) was then added dropwise. After stirring at room temperature for 8 hours, the reaction was diluted with 20 mL of ethyl acetate (20 mL), and then centrifuged (7000 rpm, 20 min). The supernatant was concentrated in vacuo and the crude residue was purified by column chromatography on silica gel (2:1 hexane:ethyl acetate) to provide isomer A (110 mg, 9.6% yield), isomer B (450 mg, 40.0% yield) and isomer C (350 mg, 30.4%). Each isomer was further purified by recrystallization from methanol.

A. (4R,4aS,7R,7aR,12bR,15R)-7,9-dimethoxy-3-methyl-1,2,3,4,7,7a-hexahydro-7,4a-(epithiomethano)-4,12-methanobenzofuro[3,2-e]isoquinoline-15-carbonitrile

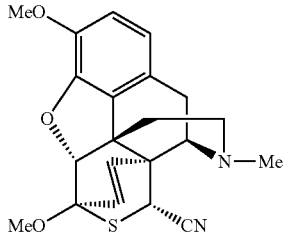 [SMILES: COc1ccc2c3c1O[C@@H]1[C@]34CCN(C)[C@H](C2)[C@]42C=C[C@@]1(OC)S[C@H]2C#N]

$R_f$=0.73 (1:1 hexane:ethyl acetate); mp 184-185° C.; $[\alpha]_D^{20}$=−319.1° (c 1.0, CHCl$_3$); $^1$H NMR (600 MHz, CDCl$_3$) δ 6.66 (d, J=8.2 Hz, 1H), 6.59 (d, J=8.2 Hz, 1H), 6.39 (dd, J=9.1, 1.3 Hz, 1H), 5.66 (d, J=9.1 Hz, 1H), 5.38 (s, 1H), 4.92 (s, 1H), 3.80 (s, 3H), 3.62 (s, 3H), 3.54 (d, J=6.6 Hz, 1H), 3.31 (d, J=18.6 Hz, 1H), 2.55 (dd, J=18.6, 6.6 Hz, 2H), 2.46-2.38 (m, 4H), 2.01-1.93 (m, 1H), 1.90 (dd, J=13.6, 2.9 Hz, 1H); $^{13}$C NMR (151 MHz, CDCl$_3$) δ 146.82, 142.22, 133.16, 131.53, 130.87, 126.86, 119.64, 119.11, 113.67, 92.26, 89.93, 59.13, 56.43, 53.88, 47.55, 45.02, 43.48, 36.10, 33.79, 22.81; IR (neat, cm$^{-1}$) v 2915, 2841, 2797, 2232, 1442, 1050, 869, 817, 795, 592; MS (EI$_+$, m/z (rel. %)): 382 (93), 311 (50), 325 (23), 296 (25), 267 (22), 255 (35), 230 (55), 58 (100); HRMS (ESI) Anal. Calcd. for C$_{21}$H$_{22}$N$_2$O$_3$S: 382.14. found 382.13.

B. (4R,4aS,7S,7aR,12bS,14S)-7,9-dimethoxy-3-methyl-1,2,3,4,7,7a-hexahydro-4a,7-(epithiomethano)-4,12-methanobenzofuro[3,2-e]isoquinoline-14-carbonitrile

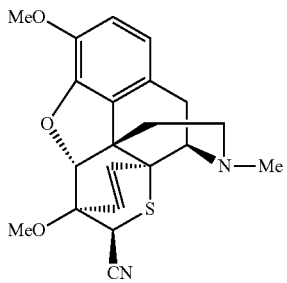 [SMILES: COc1ccc2c3c1O[C@H]1[C@@]4(OC)C=C[C@@]5(S[C@H]4C#N)[C@@H](C2)N(C)CC[C@]315]

$R_f$=0.58 (1:1 hexane:ethyl acetate); mp 145-150° C.; $[\alpha]_D^{20}$=−218.2° (c 1.0, CHCl$_3$); $^1$H NMR (600 MHz, CDCl$_3$) δ 6.65 (d, J=8.1 Hz, 1H), 6.56 (d, J=8.1 Hz, 1H), 5.91 (q, J=9.1 Hz, 2H), 5.00 (s, 1H), 3.83 (s, 3H), 3.77 (s, 1H), 3.67 (s, 3H), 3.39 (d, J=6.6 Hz, 1H), 3.27 (dd, J=18.3, 10.6 Hz, 1H), 2.93 (td, J=12.7, 5.5 Hz, 1H), 2.68 (dd, J=12.2, 5.3 Hz, 1H), 2.53-2.44 (m, 2H), 2.40 (s, 3H), 1.89 (dd, J=13.1, 2.5 Hz, 1H); $^{13}$C NMR (151 MHz, CDCl$_3$) δ 147.03, 142.51, 138.04, 133.15, 126.58, 124.61, 119.96, 117.36, 114.57, 91.42, 79.99, 60.00, 56.86, 53.97, 52.90, 50.46, 45.77, 43.41, 35.16, 32.67, 23.20; IR (neat, cm$^{-1}$) v 2935, 2836, 2792, 2234, 1499, 1279, 1107, 1021, 906, 793; MS (EI$_+$, m/z (rel. %)): 382 (7), 311 (95), 297 (50), 255 (22); HRMS (ESI) Anal. Calcd. for C$_{21}$H$_{22}$N$_2$O$_3$S: 382.14. found 382.14.

C. (4R,4aS,7S,7aR,12bS,14R)-7,9-dimethoxy-3-methyl-1,2,3,4,7,7a-hexahydro-4a,7-(epithiomethano)-4,12-methanobenzofuro[3,2-e]isoquinoline-14-carbonitrile

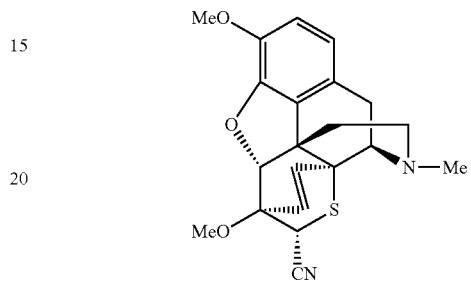

$R_f$=0.50 (1:1 hexane:ethyl acetate); mp 164-165° C. $[\alpha]_D^{20}$=+5.9° (c 1.0, CHCl$_3$); $^1$H NMR (600 MHz, CDCl$_3$) δ 6.66 (d, J=8.2 Hz, 1H), 6.58 (d, J=8.2 Hz, 1H), 6.00 (d, J=8.8 Hz, 1H), 5.95 (d, J=9.0 Hz, 1H), 4.52 (s, 1H), 4.08 (s, 1H), 3.83 (s, 3H), 3.68 (s, 3H), 3.47 (d, J=6.5 Hz, 1H), 3.26 (d, J=18.5 Hz, 1H), 2.71 (td, J=12.6, 5.5 Hz, 1H), 2.61 (dd, J=12.2, 5.3 Hz, 1H), 2.54 (dd, J=18.5, 6.6 Hz, 1H), 2.47-2.40 (m, 1H), 2.39 (s, 3H), 1.81 (dd, J=12.8, 2.7 Hz, 1H); $^{13}$C NMR (151 MHz, CDCl$_3$) δ 146.54, 142.45, 136.42, 133.13, 126.37, 126.35, 120.22, 117.77, 114.13, 90.76, 80.18, 77.25, 77.04, 76.83, 60.05, 56.61, 53.14, 52.47, 50.66, 45.58, 43.34, 35.65, 32.90, 23.16; IR (neat, cm$^{-1}$) v 2948, 2802, 2235, 1500, 1284, 1108, 1019, 894, 760; MS (EI$_+$, m/z (rel. %)): 382 (7), 311 (95), 296 (50), 255 (22); HRMS (ESI) Anal. Calcd. for C$_{21}$H$_{22}$N$_2$O$_3$S; 382.14. found 382.14.

III. Preparation of O-Demethylated Thioaldehyde Adduct Isomers

Method A: To a solution of thioaldehyde adduct isomers B and C (200 mg, 0.52 mmol) in dry CH$_2$Cl$_2$ (10 mL) was slowly added BBr$_3$ (0.780 g, 3.12 mmol) at 0° C. under an argon atmosphere. The reaction was stirred for 20 min at 0° C., removed from the ice bath and stirred for another 15 min. The reaction mixture was poured into cold water and acidity was slowly adjusted to pH=8 with 15% aqueous NaOH solution. The mixture was extracted with CH$_2$Cl$_2$. The combined organic phases were concentrated in vacuo and purified by column chromatography (1:1 hexane:ethyl acetate) yielding 0-demethylated thioaldehyde adduct isomers B and C (162 mg, 85%). The 0-demethylation of thioaldehyde adduct isomer B was also performed and was observed to give 0-demethylated thioaldehyde adduct isomer B.

Method B: To a solution of thioaldehyde adduct isomer B (150 mg, 0.4 mmol) in dry CH$_2$Cl$_2$ (15 mL) was slowly added BF$_3$.SMe$_2$ complex (0.25 mL, 2.36 mmol) at 0° C. under an argon atmosphere. The reaction was stirred for 4 hours at 0° C. and then 2 hours at room temperature. The reaction was then decanted into ice-water (20 mL) and the acidity was slowly adjusted to pH=8 with 15% aqueous NaOH solution. The aqueous layer was extracted with CH$_2$Cl$_2$ (10 mL, 3×). The organic layers were combined and then washed with brine and dried over Na$_2$SO$_4$, concentrated in vacuo, then purified by column chromatography (1:1 hexane:ethyl acetate) to yield 0-demethylated thioaldehyde adduct isomer B (74 mg, 50%).

Method C: To a solution of thioaldehyde adduct isomer B (170 mg, 0.395 mmol) in dry MeSO$_3$H (1.15 mL, 11.8 mmol) was slowly added methionine (90 mg, 0.594 mmol). The orange solution was then heated to 50° C. and left to stir for 8 hours. The reaction was monitored by HPLC. The reaction was then decanted into ice-water (20 mL) and the acidity was slowly adjusted to pH=8 with 15% aqueous NaOH solution. The aqueous layer was extracted with CH$_2$Cl$_2$ (10 mL, 3×). The organic layers were combined and then washed with brine and dried over Na$_2$SO$_4$, concentrated in vacuo, and the product purified by column chromatography (1:1 hexane:ethyl acetate) to yield 0-demethylated thioaldehyde adduct isomer B (73 mg, 51%).

Method D: To a solution of thioaldehyde adduct isomer B and/or C (110 mg, 0.287 mmol) in dry CH$_2$Cl$_2$ (5 mL) was slowly added B-I-9-BBN 1M in hexanes (0.86 mL, 0.863 mmol) at room temperature. After four hours, the reaction was then decanted into ice-water (20 mL) and the acidity was slowly adjusted to pH=8 with 15% aqueous NaOH solution. The aqueous layer was extracted with CH$_2$Cl$_2$ (10 mL, 3×). The organic layers were combined and then washed with brine and dried over Na$_2$SO$_4$, concentrated in vacuo, then purified by column chromatography (1:1 hexane:ethyl acetate) to yield 0-demethylated thioaldehyde adduct isomer B and/or C (80 mg, 72%).

B. (4R,4aS,7S,7aR,12bS,14S)-9-hydroxy-7-methoxy-3-methyl-1,2,3,4,7,7a-hexahydro-4a,7-(epithiomethano)-4,12-methanobenzofuro[3,2-e]isoquinoline-14-carbonitrile

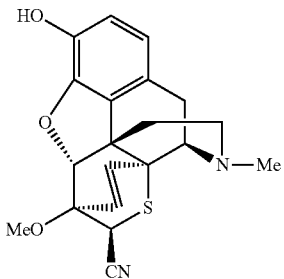 [SMILES: CO[C@]12C=C[C@@]3(S[C@H]1C#N)[C@H]1Cc4ccc(O)c5c4[C@@]3(CCN1C)[C@H]2O5]

R$_f$=0.35 (1:1 hexane:ethyl acetate); mp 145° C.; [α]$_D^{20}$=−199.2° (c 0.25, MeOH); $^1$H NMR (600 MHz, MeOD) δ 6.53 (d, J=8.1 Hz, 1H), 6.48 (d, J=8.1 Hz, 1H), 6.02-5.95 (m, 2H), 4.83 (s, 1H), 4.15 (s, 1H), 3.62 (s, 3H), 3.42 (d, J=6.6 Hz, 1H), 3.26 (d, J=18.5 Hz, 1H), 2.87 (td, J=12.7, 5.5 Hz, 1H), 2.64 (dd, J=12.2, 5.2 Hz, 1H), 2.56 (dd, J=18.5, 6.7 Hz, 1H), 2.46 (td, J=12.3, 3.7 Hz, 1H), 2.37 (s, 3H), 1.81 (dd, J=13.0, 2.8 Hz, 1H). $^{13}$C NMR (151 MHz, MeOD) δ 146.99, 140.23, 139.45, 134.10, 126.76, 124.37, 121.18, 118.94, 118.48, 92.68, 81.19, 61.23, 54.04, 53.73, 51.56, 49.85, 46.85, 43.50, 35.41, 33.71, 24.01; IR (neat, cm$^{-1}$) v 3189, 2936, 2803, 2235, 2069, 1455, 1154, 1102, 1028, 943, 905, 757; MS (EI$_+$, m/z (rel. %)): 368 (10), 297 (20), 241 (15), 184 (40); HRMS (ESI) Anal. Calcd. for C$_{20}$H$_{20}$N$_2$O$_3$S: 368.12. found 368.11.

C. (4R,4aS,7S,7aR,12bS,14R)-9-hydroxy-7-methoxy-3-methyl-1,2,3,4,7,7a-hexahydro-4a,7-(epithiomethano)-4,12-methanobenzofuro[3,2-e]isoquinoline-14-carbonitrile

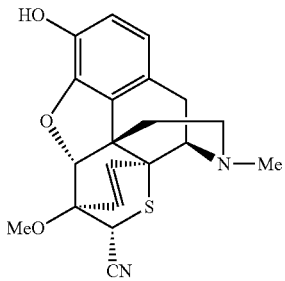 [SMILES: CO[C@]12C=C[C@@]3(S[C@@H]1C#N)[C@H]1Cc4ccc(O)c5c4[C@@]3(CCN1C)[C@H]2O5]

R$_f$=0.23 (1:1 hexane:ethyl acetate); mp 170-174° C. [α]$_D^{20}$=−1.16° (c 0.5, MeOH); $^1$H NMR (600 MHz, DMSO) δ 6.49 (d, J=8.0 Hz, 1H), 6.43 (d, J=8.0 Hz, 1H), 6.03 (d, J=8.9 Hz, 1H), 5.74 (d, J=8.7 Hz, 1H), 4.94 (s, 1H), 4.73 (s, 1H), 3.51 (s, 3H), 3.43 (d, J=6.4 Hz, 1H), 3.10 (d, J=18.4 Hz, 1H), 2.65 (td, J=12.7, 5.4 Hz, 1H), 2.57-2.45 (m, 8H), 2.27 (s, 3H), 2.26-2.20 (m, 1H), 1.63 (dd, J=12.9, 2.6 Hz, 1H); $^{13}$C NMR (151 MHz, DMSO) δ 145.16, 138.90, 136.51, 132.95, 126.83, 124.81, 119.86, 118.69, 117.13, 87.11, 79.94, 59.24, 52.50, 51.37, 50.08, 45.18, 42.84, 33.60, 32.20, 22.45; IR (neat, cm$^{-1}$) v 3509, 3358, 2926, 2803, 2241, 1638, 1497, 1112, 1030, 891, 761; MS (EI$_+$, m/z (rel. %)): 362 (10), 297 (20), 78 (90), 63 (100); HRMS (ESI) Anal. Calcd. for C$_{20}$H$_{23}$N$_2$O$_3$S: 368.12. found 368.11.

IV. Preparation of Oripavine

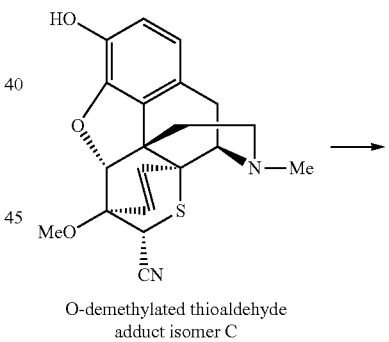

O-demethylated thioaldehyde adduct isomer C

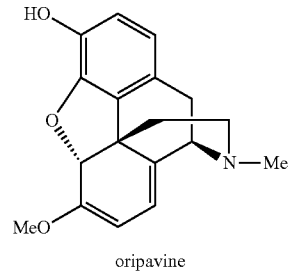

oripavine

Method E: To a solution of 0-demethylated thioaldehyde adduct isomer C (400 mg, 1.09 mmol) in DMSO (1.5 mL) was added 2,6-di-tert-butyl-4-methylphenol (BHT) (21 mg, 0.11 mmol), and 2,3-dimethylbutadiene (2.5 mL, 22.1 mmol), which was then charged to a sealed tube under argon atmosphere. The reaction was stirred vigorously for 24 hours at 75° C. The 2,3-dimethylbutadiene was removed using a rotary evaporator, and then the contents were dissolved in CHCl$_3$. The organic solution was washed with water to remove DMSO. The chloroform was then evaporated and the product purified by column chromatography (9:1 CH$_2$Cl$_2$: MeOH) to yield oripavine (210 mg, 65%). NMR spectra, R$_f$, and mp were in agreement with previously published data.[14]

Method F: To a solution of 0-demethylated thioaldehyde adduct isomer C (66 mg, 0.18 mmol) in CH$_2$Cl$_2$ (2 mL) was added mCPBA 77% (40 mg, 0.18 mmol) and the solution was left overnight with stirring at room temperature under an argon atmosphere. The CH$_2$Cl$_2$ was evaporated using a rotary evaporator, and the solid was then dissolved in 20 mL of ethanol and then heated at reflux for 2.5 hours. The ethanol was then evaporated using a rotary evaporator and the crude residue was purified by column chromatography (4:1 CHCl$_3$: MeOH) to yield oripavine (42 mg, 78%). NMR spectra, R$_f$, and mp were in agreement with previously published data.[14]

Results and Discussion

A. Demethylation of Iron Complex of Thebaine

Thebaine and iron pentacarbonyl were irradiated with ultraviolet light providing thebaine-iron tricarbonyl complex in quantitative yield. Subsequent O-demethylation was accomplished using methods A: BBr$_3$, B: BF$_3$.SMe$_2$, C: MeSO$_3$H/methionine, or D: B-iodo-9-BBN, producing the oripavine-iron tricarbonyl complex in 83%, 83%, 67%, and 63% yield respectively. The workup of the crude oripavine-iron tricarbonyl complex proved to be sensitive, decomposing upon reaching an alkaline pH, but could be accomplished by a quench with ice water and subsequent extraction of the oripavine-iron tricarbonyl complex with 10% isopropanol in dichloromethane. The purified product is not bench stable.

Different chemical methods for the decomplexation of the oripavine iron complex were tested (TMANO, CAN, CuCl$_2$, FeCl$_3$) but were not observed to provide oripavine in a useful yield. However, photolytic iron ligand exchange with MeCN[22] provided the desired compound in a 35% yield. In this method, a solution of oripavine-iron tricarbonyl complex in acetonitrile was irradiated by UV light, providing oripavine as a free base. The irradiation was stopped after 2.5 hours, while there was still starting material in the mixture because at longer irradiation times, oripavine started to decompose during the reaction.

B. O-Demethylation of Diels-Alder Adduct of Thioaldehyde

Diels-Alder cycloaddition to the electron rich diene of thebaine with an electron deficient thioaldehyde, generated in situ from the Bunte salt and triethylamine, provided three new opioid compounds, the thioaldehyde adduct isomers A-C. According to previous reports by Kirby and others[17,18,19,20,23] the thioaldehyde behaves as a strong dienophile, cyclizing with thebaine in a kinetically favored regioselective cycloaddition whereby the sulfide has connectivity to C-14 of the morphinan skeleton. Two epimers of this compound were isolated, arising presumably from epimerization of the initial cycloadduct. Kirby observed for a thioaldehyde ester system that upon continuous heating for several hours,[17] the regioisomer corresponding to thioaldehyde adduct isomer A was enriched.

The three C-ring-protected thebaine derivatives, thioaldehyde adduct isomers A-C were isolated in 80% yield after chromatography in a 1:4.2:3.2 ratio respectively. Though purified chromatographically for analytical purposes, the isolation of cycloadducts can be performed using centrifugation and filtration. The thioaldehyde adduct isomer A, the minor product, formed crystals useful for analysis by X-ray crystallography for absolute stereochemical assignment.

C-14 sulfide isomers B and C were each individually subjected to the four 3-O-demethylation procedures, A, B, C, and D, previously described, supplying the corresponding O-demethylated thioaldehyde adduct isomers B and C in in 85%, 50%, 51%, and 72% yield respectively.

Release of oripavine from the cycloadduct was accomplished by two procedures. Method E: the capture of the transient thioaldehyde by an excess of 2,3-dimethylbutadiene in a sealed tube for 8 hours at 75° C. provided oripavine in 65% yield after chromatography (4:1 CHCl$_3$:MeOH). Alternatively, method F: the sulfide adduct was oxidized with mCPBA to the sulfoxide, which was then released from oripavine by cycloreversion to provide a transient thioaldehyde S-oxide (sulfine), which was then captured irreversibly by ethanol, likely, while not wishing to be limited by theory, to form a sulfinate ester (not isolated). After evaporation of ethanol, the crude reaction mixture was chromatographed (4:1 CHCl$_3$:MeOH) to yield oripavine in 78% yield.

After characterization of the individual chemical entities in the synthesis, the sequence was repeated without separation of intermediate isomers. The reaction stoichiometry remained the same.

While the present application has been described with reference to what are presently considered to be the preferred examples, it is to be understood that the application is not limited to the disclosed examples. To the contrary, the present application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE SPECIFICATION

[1] Endoma-Arias, M. A.; Cox, D. P.; Hudlicky, T. *Advanced Synthesis & Catalysis* 2013, 355, 1869-1873.
[2] Machara, A.; Werner, L.; Endoma-Arias, M. A.; Cox, D. P.; Hudlicky, T. *Advanced Synthesis & Catalysis* 2012, 354, 613-626.
[3] US Patent Application Publication No. 2012/0046465 A1.
[4] Machara, A.; Cox, P.; Hudlicky, T. *Heterocycles* 2012, 84, 615-623.
[5] Werner, L.; Wernerova, M.; Machara, A.; Endoma-Arias, M. A.; Duchek, J.; Adams, D. R.; Cox, D. P.; Hudlicky, T. *Advanced Synthesis & Catalysis* 2012, 354, 2706-2712.
[6] Kissin, I. *Anesthesia & Analgesia* 2010, 110, 780-789.
[7] Lobmaier, P.; Gossop, M.; Waal, H.; Bramness, J. *European Journal of Clinical Pharmacology* 2010, 66, 537-545.
[8] Spetea, H.; Schmidhammer, M. *Top. Curr. Chem.* 2011, 299, 63.
[9] U.S. Pat. No. 6,067,749.
[10] U.S. Pat. No. 6,376,221.
[11] Lawson, J. A.; DeGraw, J. I. *J. Med. Chem.* 1977, 20, 165-166.
[12] Wu, H.; Thatcher, L. N.; Bernard, D.; Parrish, D. A.; Deschamps, J. R.; Rice, K. C.; MacKerell, A. D.; Coop, A. *Organic Letters* 2005, 7, 2531-2534.

[13] Sipos, A.; Berenyi, S.; Antus, S. *Helvetica Chimica Acta* 2009, 92, 1359-1365.
[14] Coop, A.; Janetka, J. W.; Lewis, J. W.; Rice, K. C. *Journal of Organic Chemistry* 1998, 63, 4392-4396.
[15] Fitton, A.; Birch, H. *Aust. J. Chem.* 1969, 22, 971-976.
[16] Kelly, L. F.; Liepa, A. J. *Tetrahedron Letters* 1985, 26, 501-504.
[17] Kirby, G. W.; Sclare, A. D. *J. Chem. Soc. Perkin Trans.* 1 1991, 2329-2338.
[18] Vedejs, E.; Perry, D. A.; Houk, K. N.; Rondan, N. G. *J. Am. Chem. Soc.* 1983, 105, 6999-7001.
[19] Bladon, C. M.; Ferguson, I. E.; Kirby, G. W.; Lochead, A. W.; McDougall, D. C. *J. Chem. Soc., Chem Commun.* 1983, 423-425.
[20] Freer, A.; Kirby, G. W.; Lewis, R. A. *J. Chem. Soc., Chem. Commun.* 1987, 718-719.
[21] Berenyi, S.; Csutoras, C.; Sipos, A. *Current Medicinal Chemistry* 2009, 16, 3215-3242.
[22] Knolker, H. J.; Goesmann, H.; Klauss, R. *Angew. Chem. Int. Ed.* 1999, 38, 702-705.
[23] Pindur, U.; Keilhofer, D. *Liebigs Ann. Chem.* 1993, 947-953.

The invention claimed is:

1. A method for the preparation of hydromorphone, comprising:
   (a) protecting oripavine under conditions to provide a ketal of Formula I:

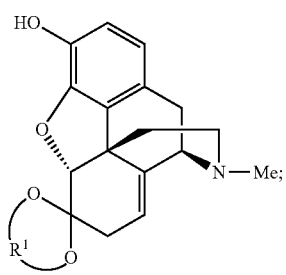

(b) reducing the ketal of Formula I under conditions to provide a ketal of Formula II:

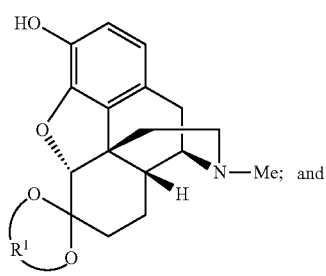

(c) deprotecting the ketal of Formula II under conditions to provide hydromorphone,
   wherein $R^1$, together with the oxygen atoms to which it is bonded, forms a hydrolysable cyclic protecting group.

2. The method of claim 1, wherein the conditions to provide the ketal of Formula I comprise adding a suitable acid catalyst to a stirred suspension or solution comprising the oripavine, a suitable difunctional alcohol and optionally a solvent and allowing the mixture to react for a time and temperature for the conversion of the oripavine to the ketal of Formula I to proceed to a sufficient extent.

3. The method of claim 2, wherein the acid catalyst is p-toluenesulfonic acid.

4. The method of claim 1, wherein the conditions to provide the ketal of Formula II comprise reacting the ketal of Formula I with hydrogen gas in a suitable solvent in the presence of a suitable hydrogenation catalyst and allowing the mixture to react for a time and temperature for the conversion of the ketal of Formula I to the ketal of Formula II to proceed to a sufficient extent.

5. The method of claim 4, wherein the hydrogenation catalyst comprises Pt/C.

6. The method of claim 1, wherein the conditions to provide hydromorphone comprise deprotecting the ketal of Formula II under suitable acidic conditions for a time and temperature for the conversion of the ketal of Formula II to hydromorphone to proceed to a sufficient extent.

7. The method of claim 1, wherein $R^1$, together with the oxygen atoms to which it is bonded, and the carbon atom to which each oxygen atom is bonded, forms a dioxolane moiety.

8. The method of claim 1, wherein the reducing and deprotecting steps are carried out as a one-pot procedure.

9. The method of claim 1, wherein $R^1$ is $C_{1-6}$ alkylene.

10. The method of claim 9, wherein $R^1$ is $C_{1-4}$ alkylene.

11. The method of claim 1, wherein the oripavine is prepared by a method comprising:
    (a) protecting the cyclohexadiene moiety of thebaine under conditions to provide a cyclohexadiene-protected thebaine;
    (b) 3-O-demethylating the cyclohexadiene-protected thebaine under conditions to provide a cyclohexadiene-protected oripavine; and
    (c) deprotecting the cyclohexadiene-protected oripavine under conditions to provide oripavine.

12. The method of claim 11, wherein the cyclohexadiene moiety of thebaine is protected by an iron tricarbonyl group and the method comprises:
    (a) protecting the cyclohexadiene moiety of thebaine under conditions to provide a cyclohexadiene-protected thebaine of Formula III:

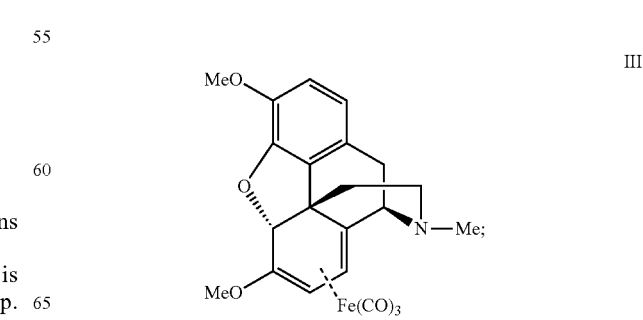

(b) 3-O-demethylating the cyclohexadiene-protected thebaine of Formula III under conditions to provide a cyclohexadiene-protected oripavine of Formula IV:

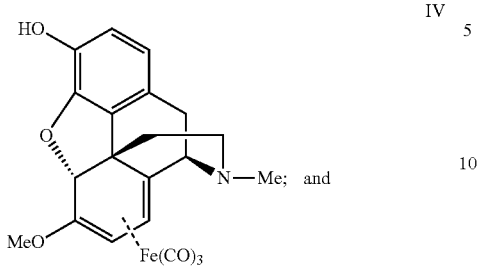

IV (c) deprotecting the cyclohexadiene-protected oripavine of Formula IV under conditions to provide oripavine.

13. The method of claim 11, wherein the cyclohexadiene moiety of thebaine is protected as a Diels Alter adduct of thioaldehyde and the method comprises:

(a) protecting the cyclohexadiene moiety of thebaine under conditions to provide one or more cyclohexadiene-protected thebaines of Formula V(a) or V(b):

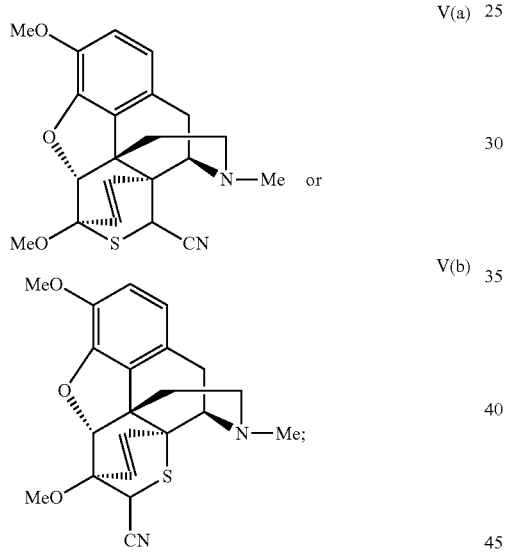

V(a)

V(b)

(b) 3-O-demethylating one or more of the cyclohexadiene-protected thebaines of Formula V(a) or V(b) under conditions to provide one or more cyclohexadiene-protected oripavines of Formula VI(a) or VI(b):

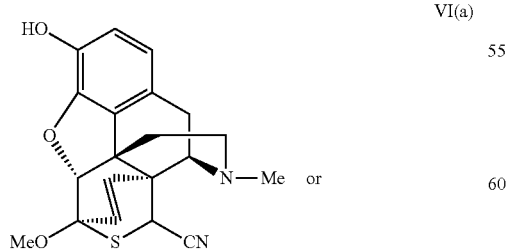

VI(a)

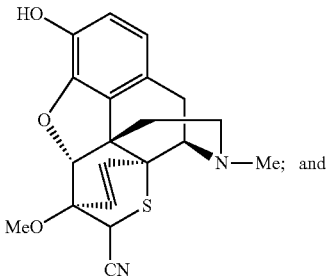

VI(b)

(c) deprotecting one or more of the cyclohexadiene-protected oripavines of Formula VI(a) and VI(b) under conditions to provide oripavine.

14. A method for the preparation of hydromorphone, comprising:

(a) protecting the cyclohexadiene moiety of thebaine under conditions to provide a cyclohexadiene-protected thebaine;

(b) 3-O-demethylating the cyclohexadiene-protected thebaine under conditions to provide a cyclohexadiene-protected oripavine;

(c) deprotecting the cyclohexadiene-protected oripavine under conditions to provide oripavine;

(d) protecting oripavine under conditions to provide a ketal of Formula I:

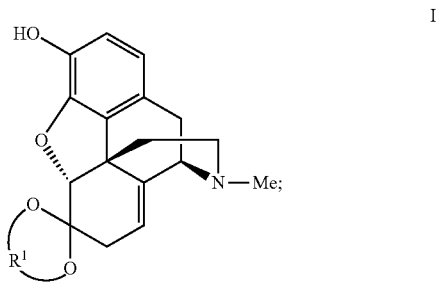

I (e) reducing the ketal of Formula I under conditions to provide a ketal of Formula II:

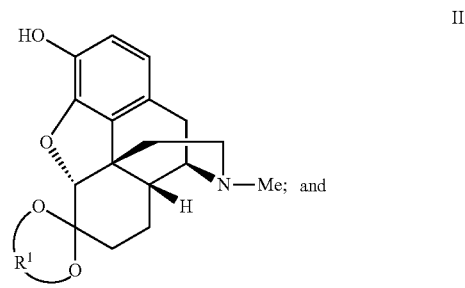

II (f) deprotecting the ketal of Formula II under conditions to provide hydromorphone, wherein $R^1$, together with the oxygen atoms to which it is bonded, forms a hydrolysable cyclic protecting group.

* * * * *

UNITED STATES PATENT AND TRADEMARK OFFICE
CERTIFICATE OF CORRECTION

PATENT NO. : 9,475,823 B2
APPLICATION NO. : 14/615892
DATED : October 25, 2016
INVENTOR(S) : Tomas Hudlicky et al.

Page 1 of 1

It is certified that error appears in the above-identified patent and that said Letters Patent is hereby corrected as shown below:

In title page,

Item (71) Applicants, line 1, delete "St. Catherines" and replace with --St. Catharines-- therefor.

Item (72) Inventors, line 1, delete "St. Catherines" and replace with --St. Catharines-- therefor.

Signed and Sealed this
Twentieth Day of December, 2016

Michelle K. Lee
*Director of the United States Patent and Trademark Office*